United States Patent [19]

Tamm et al.

[11] 4,111,051
[45] Sep. 5, 1978

[54] SAMPLING PROCEDURE AND DEVICE FOR FLAMELESS ATOMIC ABSORPTION SPECTROSCOPY

[75] Inventors: Rolf Günther Arnold Tamm; Bernhard Werner Huber, both of Überlingen, Fed. Rep. of Germany

[73] Assignee: Bodenseewerk Perkin-Elmer & Co., GmbH, Überlingen, Fed. Rep. of Germany

[21] Appl. No.: 688,789

[22] Filed: May 21, 1976

Related U.S. Application Data

[63] Continuation of Ser. No. 660,194, Feb. 20, 1976, abandoned.

[30] Foreign Application Priority Data

Feb. 20, 1975 [DE] Fed. Rep. of Germany ....... 2507260

[51] Int. Cl.$^2$ ............................................. G01N 1/14
[52] U.S. Cl. ................................................ 73/423 A
[58] Field of Search ...................... 73/423 A, 422 GC; 23/253

[56] References Cited

U.S. PATENT DOCUMENTS

| | | | |
|---|---|---|---|
| 3,192,968 | 7/1965 | Baruch et al. | 73/423 A |
| 3,508,442 | 4/1970 | Lighther | 73/423 A |
| 3,529,475 | 9/1970 | Lighther et al. | 73/423 A |
| 3,581,574 | 6/1971 | Smith | 73/423 A |
| 3,666,420 | 5/1972 | Paatzsch | 73/423 A |
| 3,800,984 | 4/1974 | Phelan | 23/253 |

*Primary Examiner*—S. Clement Swisher
*Attorney, Agent, or Firm*—Salvatore A. Giarrantana; Francis L. Masselle; Edwin T. Grimes

[57] ABSTRACT

An automatic sampling apparatus particularly adapted for flameless atomic absorption spectrometers has a turntable carrying a ring of sample containers. The turntable is rotatably mounted on a base plate which in turn is mounted for limited pivotal movement on a support. A rinse station for a sample probe is provided on the base plate adjacent the periphery of the turntable. A sample probe in the form of an elongated tube angled at one end to form a pipette-like tip is mounted for swinging movement about a transverse axis and concomitant rotation about its longitudinal axis so that, at both limits of movement about the transverse axis, the probe tip is directed generally downwardly. At one limit of probe displacement, and with the base plate at one limit of pivotal movement, the probe tip is immersed in, and discharges, rinse liquid at the rinse station; by pivotal movement of the base plate, one of the sample containers positionally replaces the rinse station and the probe tip enters the container to aspirate sample liquid therefrom. The turntable is indexed each time the base plate is pivoted from one limit of its movement to the other and back so that the rinse station is replaced sequentially by each of the sample containers. When the probe is swung to the other limit of its displacement, the tip deposits sample liquid in a sample cell, e.g., the sample port of a heated graphite atomizer. The flow of rinse liquid, and aspiration and deposit of sample liquid, is effected by means of a plurality of pumps and conduits connected in a series flow communication between a source of rinse liquid and the end of the probe tube remote from the tip. The pumps are actuated in timed relation to the movement of the probe, turntable and base plate and include an air pump which introduces a slug of air to separate the sample from the rinse liquid which normally occupies the entire fluid flow system (i.e., pumps and conduits) except for the tip end of the probe.

13 Claims, 6 Drawing Figures

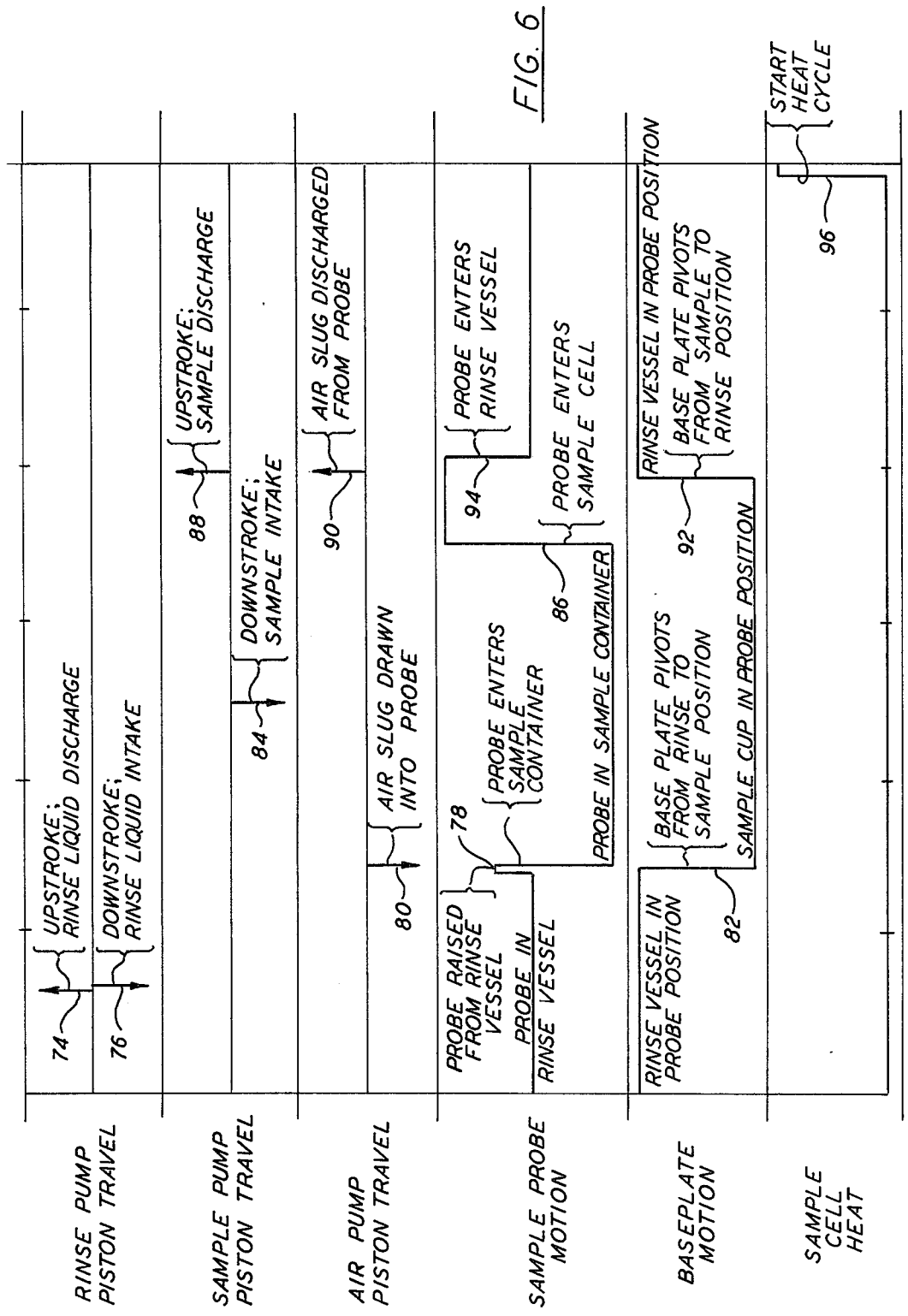

SAMPLING PROCEDURE AND DEVICE FOR FLAMELESS ATOMIC ABSORPTION SPECTROSCOPY

This is a continuation of copending application Ser. No. 660,194, filed Feb. 20, 1976 now abandoned.

BACKGROUND OF THE INVENTION

1. Field of the Invention

This invention relates to automatic sampling apparatus for analytical equipment and, in particular, to sampling apparatus for flameless atomic absorption spectrometers.

2. Description of the Prior Art

In the analysis of samples by means of atomic absorption spectroscopy, it is necessary that the sample, in liquid form, be rendered in an atomic state, i.e., to form what is often referred to in the art as an "atomic cloud". A beam of radiation of the resonance spectral line of the element to be detected is then passed through the atomic cloud to a suitable detector. As originally conceived, the atomization was carried out by spraying a nebulized vapor of the liquid sample into an open flame. In recent years, however, there has been increasing use of flameless atomization which has certain technical advantages particularly for certain elements. The most common form of flameless atomizers is a heated graphite furnace which typically takes the form of a graphite sample tube which is electrically heated by passing an electric current between electrodes disposed at the respective ends of the tube. The sample is introduced through a radial port in the wall of the tube and the spectral beam passed longitudinally through the tube.

The electrical heating current is programmed to increase in three stages so as to effect respectively drying, ashing and atomization of the sample.

At the present time, liquid samples are normally introduced manually into the sample port by means of a syringe or micro-pipette. The programmed heating of the tube is then carried out, usually automatically by means of a suitable programmable control unit: each measurement requires approximately 1 to 2 minutes. Because of the necessary manual introduction of a new sample after each individual measurement, flameless AA analysis is rather time consuming.

Whether sample introducton is effected manually or automatically, two basic requirements must be met in carrying out a series of analyses: (1) sample carryover must be avoided, i.e., the sample involved in one specific analysis must not be involved with the succeeding analysis; and (2) in view of the extremely high sensitivity of atomic absorption spectroscopy, special care must be taken to prevent contamination by dust, separating agent residues, or the like with the resultant falsification of the analytical results.

In the present state of the art, the problem of carryover is solved by the use of disposable micro-pipettes which are replaced after each sample. While this solution may be acceptable for manual sample introduction, its automatation would involve an undesirable, and perhaps unacceptably high, degree of complexity. Moreover, replacement of the micro-pipette tip does nothing to alleviate contamination which continues to be a problem.

SUMMARY OF THE INVENTION

The basic and general object of the present invention is the provision of a sampling apparatus which overcomes or mitigates at least one of the problems of the prior art as outlined hereinabove.

A more specific object is the provision of automatic sampling apparatus, particularly adapted for flameless atomic absorption analysis, which eliminates the problem of sample carryover without resort to replacement of pipette tips between each sample and which further minimizes the risk of sample contamination.

To the accomplishment of the foregoing objectives, and additional objects and advantages which will become apparent as this description proceeds, the invention contemplates an automatic sampling apparatus which comprises a sample probe having an elongate tubular portion which terminates at one end in a tip extending at an angle to the elongate portion. A probe displacement mechanism sequentially and repetitively moves the probe from a first position where the probe tip is immersed in a liquid sample or a rinsing liquid to a second position in which the tip is aligned with an aperture in a sample cell. Fluid pump and conduit means are associated with the probe for discharging a quantity of rinse liquid through the probe tip, followed by aspiration of a batch of sample liquid into the probe, both at the first probe position, and discharging the batch of sample liquid into the port of the sample cell with the probe in the second position.

In accordance with additional particular features of the invention, the automatic sampling apparatus comprises a turntable rotatably mounted on a base plate which, in turn, is mounted for limited pivotal movement on a suitable support structure. A plurality of sample containers is arranged in a concentric ring on the turntable and a rinse station for a sample probe is provided on the base plate adjacent the periphery of the turntable. A sample probe in the form of an elongated tube angled at one end to form pipette-like tip is mounted for swinging movement about a transverse axis and concomitant rotation about its longitudinal axis so that, at both limits of its movement about the transverse axis, the probe tip is directed generally downwardly.

At one limit of probe displacement and with the base plate at one limit of pivotal movement, the probe tip is immersed in, and discharges, a rinse liquid at the rinse station; by pivotal movement of the base plate, the rinse station is positionally replaced by one of the sample containers and the probe tip enters the container to aspirate sample liquid therefrom. A ratchet mechanism indexes the turntable each time the base plate is pivoted from one limit of its movement to the other and back so that the rinse station is replaced sequentially by each of the sample containers. When the probe is swung to the other limit of its displacement, the top deposits sample liquid in a sample cell, e.g., the sample aperture of a heated graphite atomizer.

The flow of rinse liquid, and aspiration and deposit of sample liquid, is effected by means of a plurality of pumps and conduits connected in series flow communication between a source of rinse liquid and the end of the probe tube remote from the tip. The pumps are actuated in timed relation to the movement to the probe, turntable, and base plate and include an air pump which introduces a slug of air into the probe tip to separate the sample from the rinse liquid which normally occupies the entire fluid flow system except for the tip end of the probe.

BRIEF DESCRIPTION OF THE DRAWINGS

FIG. 6 is a timing diagram showing the time, motion, and functional relation between various entities of the apparatus which will be referred to in explaining its operation.

DESCRIPTION OF THE PREFERRED EMBODIMENT

Figure 3:
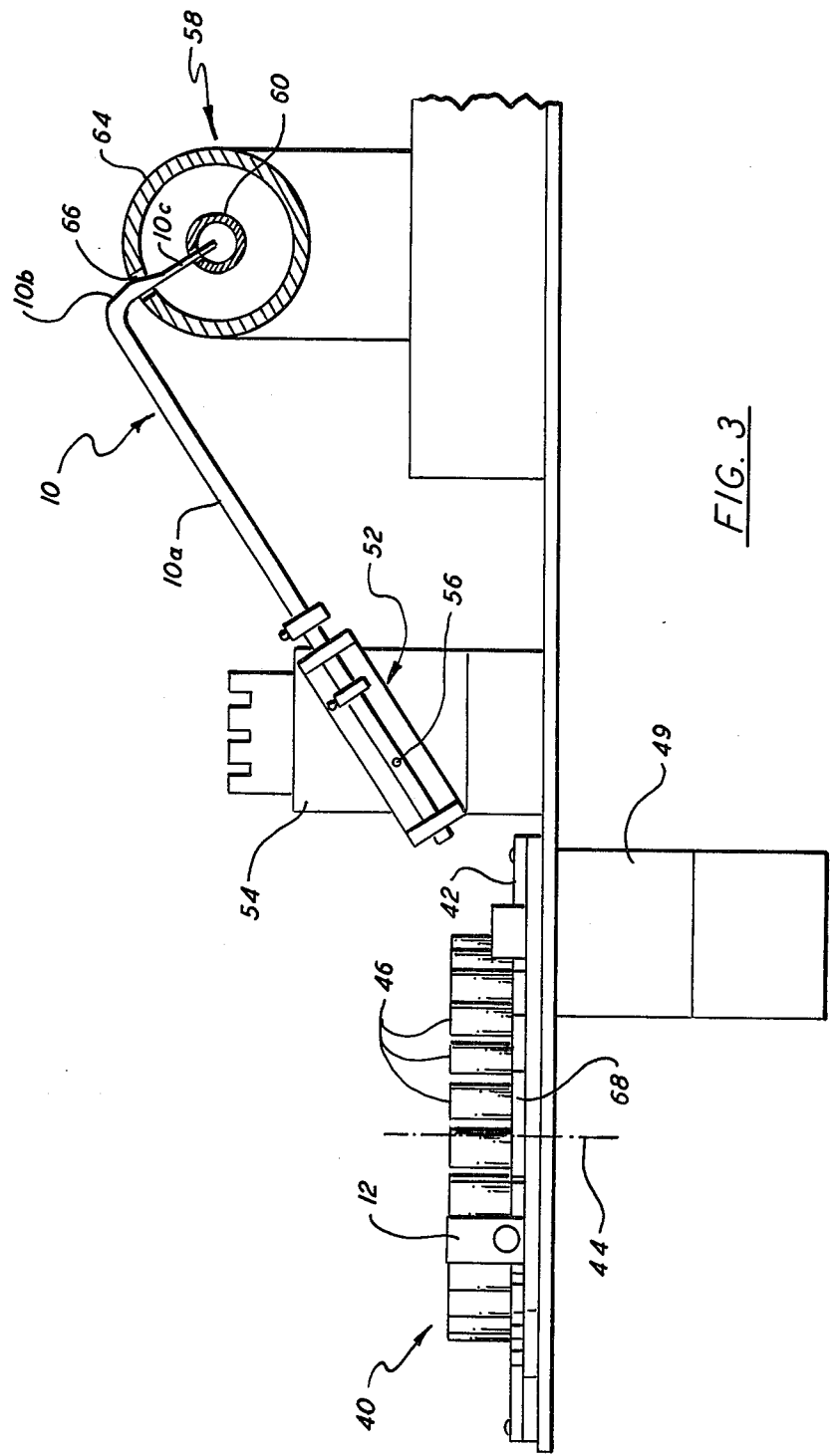
FIG. 3 is a view similar to FIG. 2 with the sample probe in position to discharge an analytical sample into a sample cell.

For convenience of description, an automatic sampling apparatus as contemplated by the present invention may be viewed as consisting of a fluid flow control system which effects the aspiration of a liquid sample and cleansing of the probe by means of a rinse liquid and a mechanical system by means of which physical motion of the sample probe and sample containers is achieved. The fluid system will be described presently with reference to FIG. 1 but first the sample probe 10 which is most clearly depicted in FIG. 3. Sample probe 10 consists of a rectilinear elongate tubular portion 10a having at one end a tip 10b making an angle of approximately 90° with the tubular portion 10a. While the tip 10b is shown to be angled at approximately 90°, the precise angle obviously is not in any way critical. The free end of tip 10b is necked down to form a pipette-like capillary 10c. In a manner which will be fully explained as this description proceeds, probe 10 is mounted cantilever fashion for swinging motion about an axis perpendicular to the length of its tubular portion 10a and for rotation about the longitudinal axis of that tubular portion.

Figure 1:
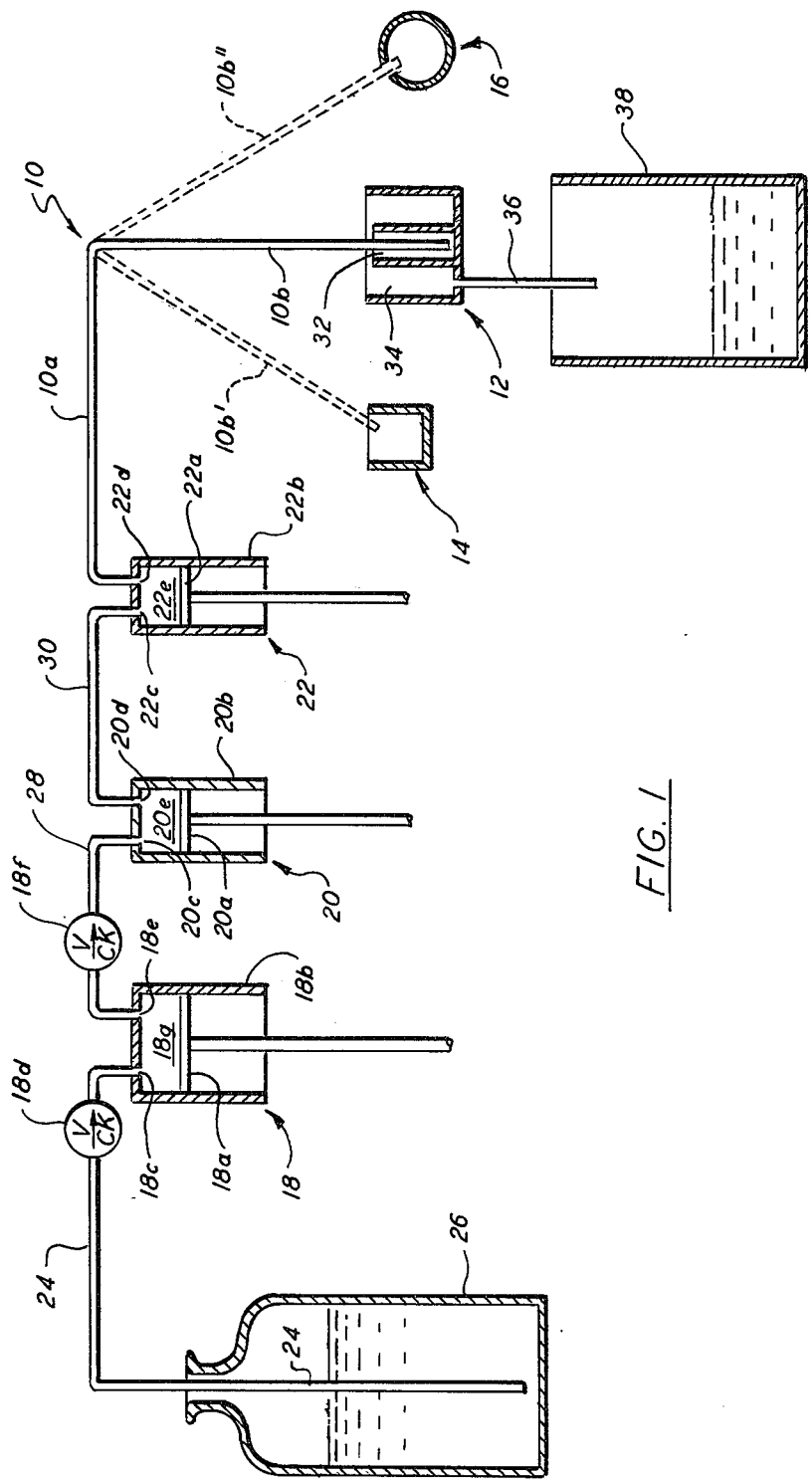
FIG. 1 is a schematic representation of the pumps and flow conduits for effecting aspiration of sample liquid and rinsing of the sample probe in accordance with the present invention.
Figure 2:
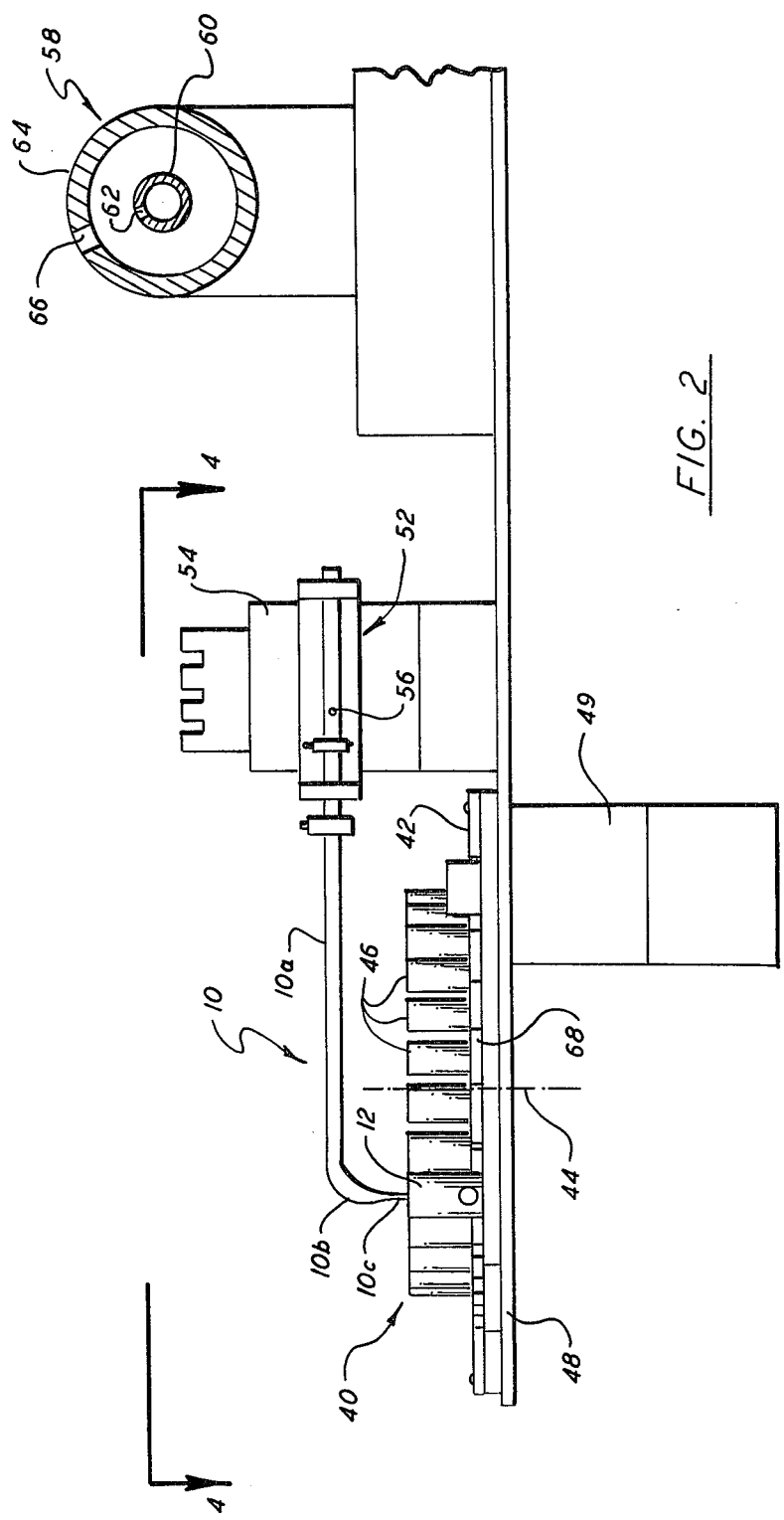
FIG. 2 is a schematic elevational view of a mechanical arrangement including a sample probe for transferring a liquid analytical sample from a sample container to a sample cell with the probe in position over the sample container.

For ease of illustration in FIG. 1, the tubular portion 10a of the probe is shown by a stationary horizontal line and the position attainable by movement of the probe represented by showing the tip 10b in three alternative positions: at 10b, shown in solid line, where the tip is in a rinsing vessel 12; in a broken line position 10b' where the probe tip is positioned to aspirate a liquid sample from a sample cup 14; and in a dotted line position 10b'' in which the tip is disposed to deposit a sample in a sample cell 16. The fluid system includes a rinse pump 18 consisting of a plunger or piston 18a operating in a cylinder 18b; an air pump 20 made up of a piston 20a operating in a cylinder 20b; and a sample pump 22 consisting of a piston 22a operating in a cylinder 22b. Reciprocation of the pistons in their respective cylinders is effected by a suitable means, such as motor-driven cams, not shown. Rinse pump 18 is by far the largest of the three and would have, for example, a full-stroke volume displacement of 1500 microliters as compared to 10 microliters for air pump 20 and 20 microliters for sample pump 22.

Each of the pump cylinders contain respective pairs of ports in communication with the working space. In the case of rinse pump 18, one port is a unidirectional flow inlet port 18c containing a check valve 18d or the like and the other a unidirectional flow outlet port 18c similarly controlled by a check valve 18f or the like. Inlet port 18c is flow-coupled by means of a conduit 24 to a source of rinse liquid represented by container 26. Outlet port 18e is connected via a conduit 28 to one of the ports (20c) of air pump 20, the other port (20d) of which is coupled via a conduit 30 to one of the ports (22c) of sample pump 22. The other port (22d) of sample pump 22 is flow-coupled to probe 10 via the end of tubular member 10a remote from tip 10b. Thus, it will be appreciated that air pump 20 and sample pump 22 are connected in series flow communication between the outlet port 18e of rinse liquid pump 18 and probe 10.

On the downward stroke of rinse pump piston 18a, rinse liquid is drawn from container 26 to fill the working space 18g of the pump and on the upward stroke of the piston 18a, rinse liquid is forced out of outlet port 18e and sequentially through conduits 28, 30 and working spaces 20e and 22e of pumps 20 and 22, respectively, and through probe 10. In operation, the entire flow system, i.e., the conduits and working spaces of the three pumps and all or most of the probe (depending on the precise point of the cycle under consideration) is filled with rinse liquid. The general flow of rinse liquid is in the direction from the source 26 to the probe 10; therefore, there is no opportunity for contaminants to be drawn into the system and any air bubbles which might be present would be flushed out.

In the solid line position, probe tip 10b is located at a rinsing station which includes a suitable vessel 12 for the containment of rinse liquid. The vessel is compartmented to form an inner chamber 32, into which the probe tip projects when positioned at the rinse station, and a surrounding outer chamber 34 which is provided with a drain 36 leading to a waste receptacle 38, drain line or the like. In a manner which will be explained presently and as previously mentioned, the probe tip can occupy an alternative position, shown in dotted line at 10b', in which it extends into sample container 14 and 10b'' in which it is aligned with an aperture 40 in sample cell 16.

From the structure thus far described, it will be appreciated that on a downward stroke of the piston of rinse pump 18, rinse liquid is drawn in through conduit 24 and valve 18d to fill the working space 18g (typically with 1500 microliters of rinse liquid for a full stroke). On the upward stroke, the rinse liquid in working chamber 18g is forced out through valve 18f and conduit 28 into and through the working space 20e of air pump 20; through conduit 30; and into and through the working space 22e of sample pump 22 into and through probe 10. With the probe at the rinse station, rinse liquid ejected through the probe tip fills inner chamber 32 and overflows into outer chamber 34 from which it flows to the waste container or drain. This accomplishes the rinsing of both the interior and exterior of the probe.

In the complete normal operation of the apparatus, as will be described in due course, probe 10 is removed from the rinse station for displacement to sample container 14, for aspiration of sample liquid. During this interval, the piston of air pump 20 moves downwardly, causing a retraction of 10 microliters of the rinse liquid in conduit 30 and probe 10; as the probe tip is out of the rinse vessel, a like volume of air is drawn into the tip of the probe. On the upward stroke of piston 20a, the rinse liquid is restored to conduit 30 and the probe, expelling the air. Similarly, a full downward stroke of the piston of sample pump 22 draws 20 microliters of rinse liquid from probe 10 and restores it on the upward stroke.

The mechanism for effecting probe motion to transfer samples will now be described with continued reference to FIGS. 2–5. The apparatus employs a carousel-type sample platter consisting of a turntable 40 mounted on a base plate 42 for rotation about a vertical axis 44. Mounting on base plate 42, adjacent the periphery of turntable 40, is rinse vessel 12. The turntable carries a ring of sample cups 46 concentric with its axis of rotation. Base plate 42 is mounted on a supporting structure 48 for pivotal movement, as by means of servo motor 49, about an axis 50 parallel to and spaced from the turntable axis between two limit positions defined by suitable abutments R & S shown in FIGS. 4 and 5. The tubular portion 10a of the sample probe is supported cantilever fashion at the end remote from its tip 10b by means of a suitable mounting 52 which permits rotation of the probe about its longitudinal axis. Any suitable means, not shown in detail, can be provided to effect this rotary movement which normally involves rotation through an angle of 180°.

Probe mounting member 52 is in turn mounted for rotation by a servo motor 54 about an axis 56 perpendicular to the longitudinal axis of the probe and remote from the probe tip end. The probe mounting arrangement, including servo motor 54, is disposed between the sample turntable 40 and a sample cell 58 which in the disclosed embodiment, takes the form of a heated graphite atomizer having a sample tube 60 disposed with its longitudinal axis horizontal and a substantially parallel to the transverse swinging axis 56 of the probe. Sample tube 60 contains an aperture 62 through which a sample may be introduced into its interior, the aperture facing upwardly at an angle of about 45° to the vertical. As is typical of such sample cells, the tube is surrounded by a housing 64 having an aperture 66 aligned with aperture 62 in the tube.

As a result of the mounting of the probe, actuation of servo motor 54 causes a swinging motion about transverse axis 56; concomitantly, the probe is rotated through 180° about its longitudinal axis. As a result, in one of its limit positions, shown in FIG. 2, the tip end of the probe overlies the base plate and at the other limit position (FIG. 3), the sample cell, and in both positions, the tip of the probe is directed downwardly. In the sample cell position, the tip of the probe is aligned with and projects through apertures 66 and 62 in the housing and sample tube respectively. In its other position, the probe tip moves to a predetermined location over the base plate.

Figure 4:
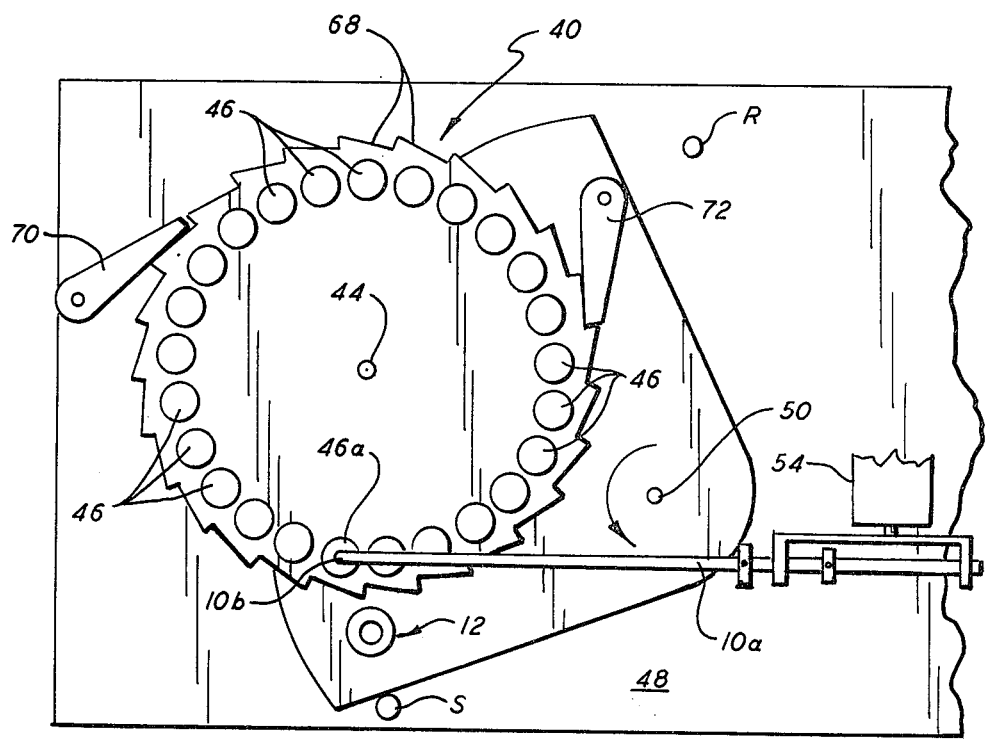
FIG. 4 is a partial plan view of the structure shown in FIG. 2 as indicated by the line 4—4.
Figure 5:
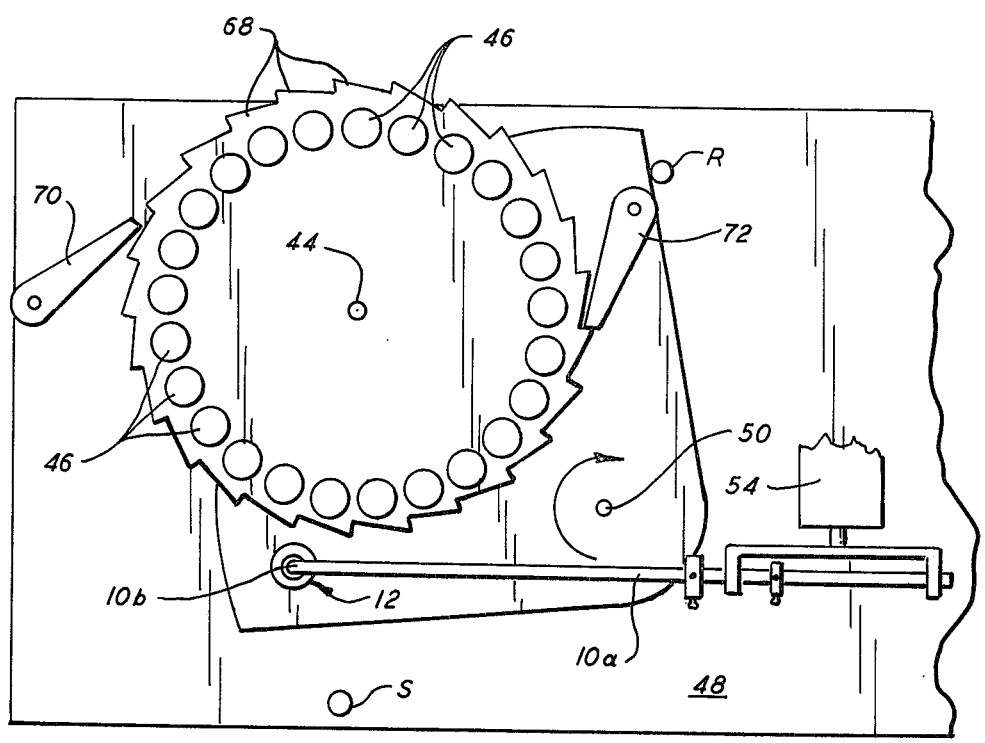
FIG. 5 is a view similar to FIG. 4 with the probe in position at the rinsing station.

Referring now to FIGS. 4 and 5 and first in particular to FIG. 4, when base plate 42 is at the limit position defined by abutment S, the predetermined location referred to is occupied by one of the sample cups (46a) on the turntable. Consequently, under these conditions, probe tip end 10c enters that particular sample cup and is in a position to effect aspiration of a batch of sample. When base plate 42 is pivoted about its axis to the limit position defined by abutment R (FIG. 5), the predetermined location formerly occupied by a sample cup is positionally replaced by the rinsing vessel 12 and under these conditions, probe tip end 10c enters the rinsing vessel instead of a sample container.

The pivotal displacement of base plate 42 preferably is utilized to effect a stepwise precession or indexing of turntable 40 so that, with each complete pivotal excursion of the base plate, i.e., from limit S position to R and back, one step of the turntable is produced. In this manner, each of the sample cups 46 in its turn is moved into the predetermined location. To this end, the periphery of turntable 40 is formed with a continuous series of teeth 68 so as to form a ratchet wheel. Adjacent one point on the periphery of the turntable ratchet, a driving or active pawl 70 is mounted for pivotal movement on support structure 38; at another point, a locking pawl 72 is mounted for pivotal movement on the base plate. Thus, it will be seen that as the base plate pivots about its axis 50 in a counterclockwise direction, driving pawl 70 engages one of the ratchet teeth and causes clockwise rotation of the turntable. Locking pawl 72 during this motion simply rides over the ratchet wheel and, on the return or clockwise motion of the base plate, engages a tooth to prevent regression of the turntable.

It will be understood that the servo motor 59 provided to achieve the pivotal movement of the base plate on the supporting structure and servo motor 54 for effecting probe motion as well as motor for driving the cams or other means employed for reciprocation of the fluid system pistons are operated in a predetermined correlation and time sequence to effect the overall operation of the apparatus. As the manner in which this is accomplished is well within the skill of the art and forms no part of the present invention, these details have been omitted from this description. However, the required correlation is illustrated in the timing diagram of FIG. 6 to which reference is now made. Arbitrarily, the condition of the apparatus shown in FIG. 5, in which the probe tip is at the rinsing station and immersed in the container of rinsing fluid will be taken as the starting point of the cycle. And it will be assumed that the rinse pump has been actuated at least one time to fill the entire fluid system and the rinsing vessel with rinse fluid. Under these conditions, the first incident (point 74 of the timing diagram) of operation is an upstroke of the rinse pump piston; as the fluid conduits and working chambers are entirely filled with rinse liquid, this upstroke causes a discharge of rinse fluid from the probe tip into the inner chamber 32 of rinsing vessel 12. The excess thus produced in the inner chamber overflows into outer chamber 34 and passes waste. In this manner, both the interior and exterior of the probe tip are cleansed of the residue from any prior use.

Rinse pump piston 18a then makes a downstroke (point 76) to refill the rinse pump working chamber 18g by aspiration of rinse liquid from source 26 through conduit 24 and inlet check valve 18d. During this downstroke, outlet port check valve 18f obviously precludes return of rinse liquid occupying the other pumps, conduits and the probe. As this time, designated by point 78 on the timing diagram, the probe is raised from the rinse vessel and air pump piston 20a moves downwardly (point 80) to cause aspiration of a small quantity (i.e., 10 microliters) of air forming a slug or bubble in the tip of the probe. During this interval, the base plate, which had been in the rinsing position, i.e., engaging limit stop R, is moved to the other limit against stop S as indicated at point 82 in the base plate motion portion of the timing diagram. Immediately thereafter, the probe descends again and the tip enters the particular sample cup occupying the predetermined location. With the probe tip in the sample container, the plunger of the sample pump moves downwardly (point 84) aspirating its displacement volume, e.g., 20 microliters, of rinse liquid causing further retracting of the rinse liquid in the probe and effecting aspiration of a corresponding volume of the sample liquid, which is separated from the rinse liquid by the air slug.

Sample take-up completed, the servo motor 54 controlling the sample probe is energized at point 86 on the timing diagram swinging the probe about its transverse axis which, with concomitant rotation of the probe about its longitudinal axis as previously explained, causes the probe tip to align with and enter the apertures of the sample cell. This accomplished, the sample pump piston moves upward (point 88) to discharge the sample and the air pump piston moves upward (point 90) to discharge the air slug. At approximately this time (point 92), the base plate pivots from its sample position to its rinse position so that with the return of the probe, the probe tip enters the rinse vessel (point 94) and the initial rinsing cycle repeated. During the rinse cycle, the heating current is applied (point 96) to the graphite furnace to commence analysis by means of a suitable switch (not shown) which may be programmed to produce the desired sequence of heating events and be activated by the same control unit employed to effect the operation of the probe displacement and pumping systems.

While there has been described hereinabove a sampling apparatus constituting an examplary embodiment of the invention, various modifications and other applications and adaptions of the invention will be apparent to persons conversant with the art.

What is claimed is:

1. In combination with a flameless atomic absorption atomizer having a heated sample cell containing an aperture for the introduction of a liquid sample, an automatic sample, an automatic sample transfer apparatus comprising:
    a. a sample probe having an elongate tubular portion terminating at one end in a tip extending at an angle to the elongate portion;
    b. a probe displacement mechanism for sequentially and repetitively moving said probe from a first position, where the probe tip is immersed in a liquid sample or rinsing liquid to a second position in which the tip is aligned with said aperture; and
    c. fluid pump and conduit means associated with said probe for discharging a quantity of rinse liquid through the probe tip, followed by aspiration of a batch of sample liquid into the probe, both at said first position, and discharging said batch of sample liquid into said aperture with the probe in said second position;
    d. said rinse liquid being introduced into the probe by said pump and conduit means via the end of the probe's tubular portion remote from said tip; and
    e. said pump and conduit means causing aspiration of a slug of air into the probe before aspiration of the sample liquid.

2. The combination defined in claim 1 wherein said pump and conduit means cause the air slug to be expressed from the probe tip following discharge of the sample batch therefrom.

3. The combination defined in claim 1 wherein said pump and conduit means include:
    a. a rinse liquid pump having unidirectional-flow inlet and outlet ports; and
    b. a sample pump having a first port flow-coupled to said remote end of the probe's tubular portion and a second port in flow communication with the outlet port of the rinse liquid pump.

4. The combination defined in claim 1 including:
    a. a rinse liquid pump having unidirectional-flow inlet and outlet ports;
    b. an air pump and a sample pump each having first and second ports; and
    c. conduits connecting said ports to place said air pump and sample pump in series flow communication between the outlet port of said rinse liquid pump and said remote end of the probe's tubular portion.

5. The combination defined in claim 1 wherein said pump and conduit means comprise:
    a. a rinse liquid pump having a unidirectional-flow inlet port, adapted to be connected to a source of rinse liquid, and a unidirectional flow outlet port;
    b. a sample pump having a pair of ports one of which is flow-coupled to said remote end of the probe's tubular portion;
    c. an air pump having a pair of ports; and
    d. fluid conduits connecting the ports of the air pump respectively to the outlet port of the rinse pump and the other port of the sample pump, said conduits and the working space of said pumps being normally completely filled with the rinse liquid during operation.

6. In combination with a flameless atomic absorption atomizer having a heated sample cell containing an aperture for introduction of a liquid sample, an automatic sample transfer apparatus comprising:
    a. a sample probe having an elongate tubular portion terminating at one end in a tip extending at an angle to the elongate portion:
    b. a probe displacement mechanism for sequentially and repetitively moving said probe from a first position, where the probe tip is immersed in a liquid sample or rinsing liquid to a second position in which the tip is aligned with said aperture;
    c. fluid pump and conduit means associated with said probe for discharging a quantity of rinse liquid through the probe tip, followed by aspiration of a batch of sample liquid into the probe, both at said first position, and discharging said batch of sample liquid into said aperture with the probe in said second position;
    d. means mounting said sample probe for rotary movement about the longitudinal axis of its elongate tubular portion;
    e. means for rotating said mounting means, and concomitantly, swinging said sample probe about a second axis perpendicular to the first said axis of the tubular portion and located at a point remote from said probe tip; and
    f. means for rotating said probe through an angle of substantially 180° around said first axis in conjunction with rotation of the probe mounting means about said second axis.

7. The combination defined in claim 6 wherein said tubular portion of the probe is rectilinear and the tip terminates in a capillary.

8. The combination defined in claim 7 further comprising:
    a. a support structure;

b. a base plate mounted on said support structure for pivotal movement about a base plate axis between two limit positions angularly spaced from one another with respect to said axis;

c. a turntable mounted on said base plate for rotation about a turntable axis substantially parallel to and spaced from said base plate axis;

d. a ring of sample containers on said turntable concentrically disposed about the turntable axis;

e. a rinsing station including a vessel for rinsing liquid, disposed on said base plate adjacent the perimeter of said turntable, said rinsing station being so located with respect to said turntable and base plate axes, the limit positions, and the ring of sample containers that, with the base plate in one of said limit positions, the rinsing station occupies a predetermined location coinciding with said first position of the probe and, in the other limit position, said location is occupied by one of said sample containers; and f. means for indexing said turntable about said turntable axis so that, with the base plate in said other position, the sample cups are moved sequentially into said predetermined location.

9. Apparatus according to claim 8 wherein said indexing means includes:

a. a series of ratchet teeth on the periphery of the turntable forming a ratchet wheel thereon;

b. a pawl pivotally mounted on said base plate adjacent the periphery of the turntable to engage the ratchet teeth 24 one point of such periphery; and c. a second pawl pivotally mounted on the support structure adjacent the periphery of said turntable and engaging the ratchet teeth at another point on such periphery.

10. Automatic sampling apparatus for an analytical instrument having a sample cell, comprising:

a. a support structure;

b. a base plate mounted on said support structure for pivotal movement about a vertical axis between two limit positions angularly spaced from one another with respect to said axis;

c. a turntable mounted on said base plate for rotation about a second axis substantially parallel to and spaced from said first axis;

d. a ring of sample containers on said turntable concentrically disposed about said second axis;

e. a rinsing station, including a vessel for rinse liquid, disposed on said base plate adjacent the perimeter of said turntable, said rinsing station being so located with respect to said axes, limit positions, and the ring of sample containers that, with the base plate in one of said limit positions, the rinsing station occupies a predetermined location and in the other limit position, said location is occupied by one of said sample containers;

f. means for indexing said turntable about said second axis so that, with the base plate in said other position, the sample cups are moved sequentially into said predetermined location;

g. a sample probe including an elongate tubular portion terminating at one end in a reduced diameter tip extending at an angle to the elongate portion;

h. means for rotatively displacing said probe about an axis transverse to the longitudinal portion thereof and remote from said probe tip between a first position in which the tip end of the probe substantially overlies said predetermined location and a second position in which the tip end of the probe substantially overlies the sample cell; and i. means for rotating the probe through an angle of substantially 180° about the longitudinal axis of its tubular portion in conjunction with rotation of the probe about said transverse axis whereby said probe tip is directed downwardly with the tip end of the probe in both said first and said second positions and said tip is directed into the sample cell in said second position; and j. means for pivoting said base plate about said first axis between said limit positions whereby, when said probe is rotated to said first position, it enters the rinsing vessel or sample container occupying said predetermined location as determined by the limit position of the base plate.

11. Apparatus according to claim 10 wherein said indexing means includes:

a. a series of ratchet teeth on the periphery of the turntable forming a ratchet wheel thereof;

b. a pawl pivotally mounted on said base plate adjacent the periphery of the turntable to engage the ratchet teeth on one point of such periphery; and c. a second pawl pivotally mounted on the support structure adjacent the periphery of said turntable and engaging the ratchet teeth at another point on such periphery.

12. An automatic sampling device comprising:

a sample probe including an elongate tubular portion terminating at one end in a reduced diameter tip extending at an angle to the elongate portion;

means mounting said probe for rotary movement about the longitudinal axis of the tubular portion;

means for rotating said mounting means and, concomitantly, said probe about a second axis perpendicular to the first said axis of the tubular portion and located at a point remote from said tip; and means for rotating said probe through an angle of substantially 180° around said first axis in conjunction with rotation of the probe about said second axis.

13. A device according to claim 12, wherein said probe tip makes an angle of approximately 90° with said tubular portion and terminates in a capillary.

* * * * *